United States Patent

Garcia-Rubio et al.

[11] Patent Number: 5,907,108
[45] Date of Patent: May 25, 1999

[54] CONTINUOUS SAMPLING AND DILUTION SYSTEM AND METHOD

[75] Inventors: Luis H. Garcia-Rubio, Temple Terrace; Francisco Lanza, Tampa; Paul J. Sacoto, St. Petersburg, all of Fla.

[73] Assignee: University of South Florida, Tampa, Fla.

[21] Appl. No.: 08/921,888

[22] Filed: Aug. 25, 1997

Related U.S. Application Data

[60] Provisional application No. 60/024,533, Aug. 26, 1996.

[51] Int. Cl.$^6$ .............................. G01N 1/18; G01N 15/06
[52] U.S. Cl. .................... 73/863.21; 73/28.01; 73/31.02; 73/31.03; 73/53.07; 73/61.41; 73/61.71; 73/863; 73/863.61
[58] Field of Search .............................. 73/1.06, 28.01, 73/31.01, 31.02, 31.03, 53.07, 61.41, 61.42, 61.71, 863, 863.21, 863.61

[56] References Cited

U.S. PATENT DOCUMENTS 5,054,309  10/1991  Mettes et al. ............................ 73/1.03
5,509,292  4/1996  D'Appollonia et al. ................. 73/1.06

FOREIGN PATENT DOCUMENTS 370151  5/1990  European Pat. Off. ................ 73/1.03
370870  5/1990  European Pat. Off. ................ 73/1.03

*Primary Examiner*—Daniel S. Larkin
*Attorney, Agent, or Firm*—Allen, Dyer, Doppelt, Milbrath & Gilchrist, P.A.

[57] ABSTRACT

A system and method for the automatic sampling and dilution of homogeneous particle dispersions is developed that uses a multistep parallel dilution network system for the sample and diluent and includes variable dilution capabilities. The sample and diluent are combined and allowed to mix uniformly over a predetermined conduit length. Resampling from the first dilution step and recombining with another diluent line results in a second dilution step. The number of steps determines the dilution range; the manipulation of the sample and diluent flow rates provides a variable dilution ratio at each dilution step. An exemplary embodiment reduces the concentration of a latex sample for analysis with uv-vis spectrometry. In another embodiment, the emulsion polymerization of styrene is followed in real time with turbidity measurements taken on diluted samples.

16 Claims, 4 Drawing Sheets

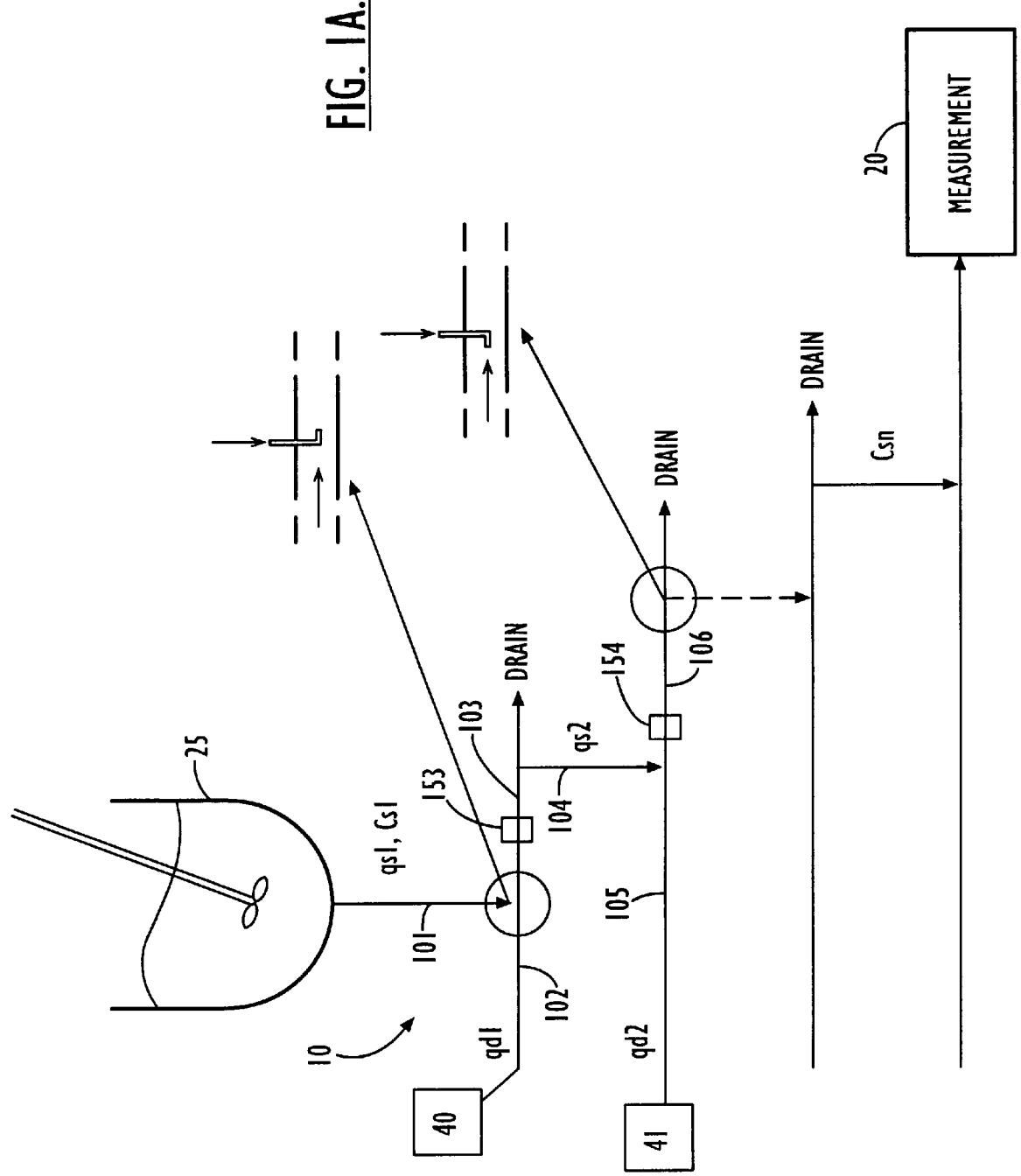

ns and Methods

CONTINUOUS SAMPLING AND DILUTION SYSTEM AND METHOD

BACKGROUND OF THE INVENTION

1. Cross-Reference to Related Application

This application claims priority from previously filed provisional application, Ser. No. 60/024,553, "Continuous Sampling and Dilution System and Method," filed Aug. 26, 1996.

2. Field of the Invention

The present invention relates to systems and methods for the characterization of particle dispersions, and, more particularly, to sampling and dilution systems and methods for the characterization of concentrated particle dispersions.

3. Description of Related Art

Analytical measurements of particle dispersions frequently require dilution in order to eliminate particle-particle interactions as an element in the analysis. For example, in light scattering measurements, it is desirable to operate in the regime in which single-particle scattering approximations are valid. It is also desirable to operate within the linear range of the analytical instrumentation, typically of the order of milligrams per cubic centimeter, for performing static and dynamic light scattering, spectroscopy, and particle counting.

On-line methods for the characterization of particle dispersions containing, for example, micrometer- and submicrometer-sized particles are important in understanding particulate systems in general, a particular example of which is colloidal systems. While on-line detection systems have been disclosed for performing measurements on such dispersions, the sampling problem remains to be addressed effectively.

The main problems in the design of an on-line dilution system arise from:

1. Difficulties in obtaining a representative sample;
2. Sample transportation delays;
3. The residence time necessary in the dilution vessel to homogenize the sample and diluent in the appropriate proportions; and
4. The time required for the measurement.

For stable homogeneous emulsions, for example, a representative sample of the process can be obtained. The transportation lags can be minimized, and accounted for, by bringing the dilution and detection system as close as possible to the process.

However, given the high dilution ratios required for techniques such as light scattering and other spectroscopic methods (approx. 1:75,000 to 1:400,000), large volumes of diluents, and therefore comparatively long residence times in the dilution vessels, are required.

Automatic on-line dilution has been performed in serial fashion in previously disclosed systems; however, none of these systems permits continuous sampling and dilution, and the serial nature creates a process in which the sampling, transportation, dilution, and measurement times are additive. As a time delay is introduced between sequential measurements, the sampling residence time increases, which biases the interpretation of the data. For example, in turbidity measurements, errors in estimates of particle concentration and particle size distribution can occur. These errors can take the form of data shifts in time relative to the sample populations existing in the sampling vessel and a loss in resolution caused by an averaging of the data over the dilution interval. Another disadvantage of serial systems is the large volume of diluent required, which is dependent upon the number of dilution steps, the volume of the mixing chamber(s), and the process flow rate.

Among the dilution systems reported are those disclosed by Ponnuswamy et al. (*J Polym. Sci.* 32, 1986), Nicoli and Elings (U.S. Pat. No. 4,794,806), Kourti and MacGregor (*ACS Symp. Ser.* 472, Chapter 3, 1991), Leiza et al. (*Proc. Control Qual.* 4, 197, 1992), Hashizame et al. (U.S. Pat. No. 5,221,521), and White (U.S. Pat. No. 5,297,431).

SUMMARY OF THE INVENTION

It is therefore an object of the invention to provide a sampling and dilution system and method capable of achieving a rapid and homogeneous dilution of a concentrated sample.

It is another object to provide such a sampling and dilution system having a variable dilution ratio and flow rate at each dilution step.

It is a further object to provide such a sampling and dilution system and method integratable with analytical instrumentation for online measurement of particle characteristics.

It is an additional object to provide a sampling and dilution system and method that retains the integrity of the sample.

It is yet another object to provide such a sampling and dilution system operable in a time sufficiently small that a reaction such as a polymerization reaction can be followed in real time.

These objects and others are achieved by the automatic sampling and dilution system of the present invention, which is capable of reducing particle concentrations several orders of magnitude in approximately 1 second.

The system comprises a multistep parallel dilution network having variable dilution capabilities. The sample, which may be taken from a reaction vessel, for example, and diluent are combined and allowed to mix uniformly over a predetermined conduit length in a first dilution step. Resampling from the first dilution step and recombination with another diluent line comprises a second dilution step. The number of steps thus determines the dilution range, and the manipulation of the sample and diluent flow rates provides a variable dilution ratio at each dilution step.

BRIEF DESCRIPTION OF THE DRAWING

FIG. 1A is a schematic of the automatic continuous sampling and dilution system with variable dilution capabilities.

DETAILED DESCRIPTION OF THE PREFERRED EMBODIMENTS

Figure 1B:
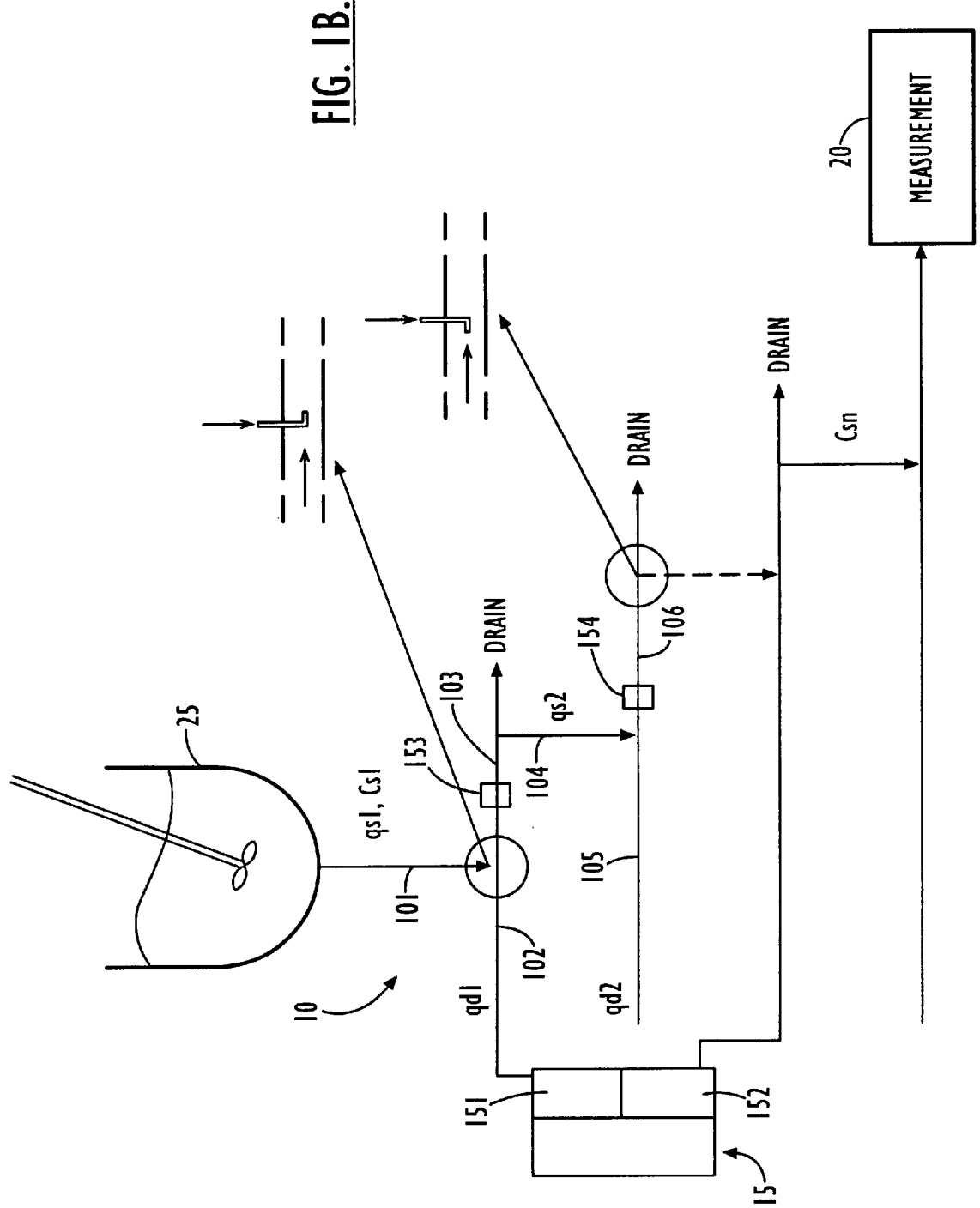
FIG. 1B is a schematic of an alternate embodiment of FIG. 1A using a unitary pump to control diluent inflow.
Figure 2:
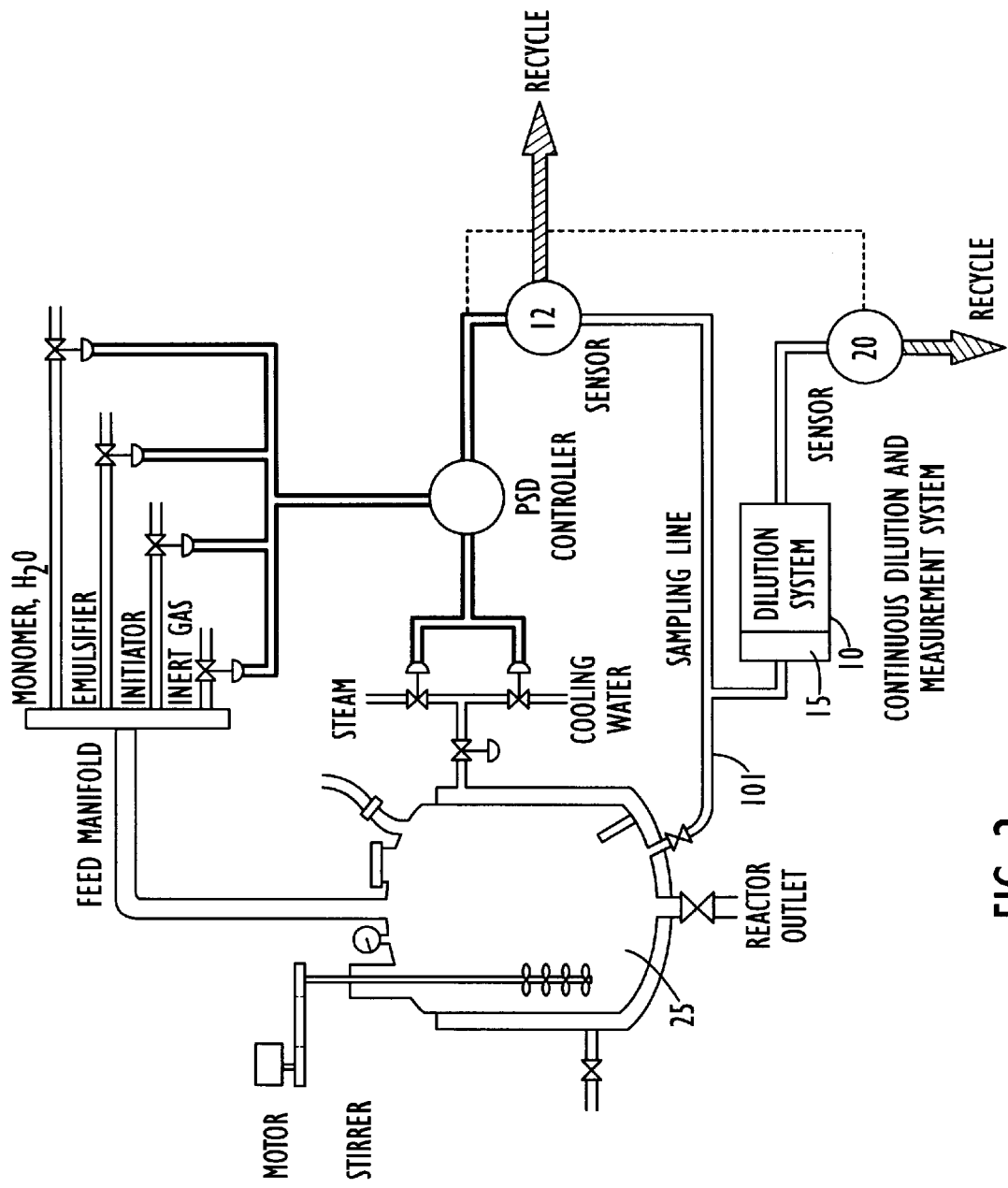
FIG. 2 is a schematic of an exemplary particle characterization layout including the dilution system integrated with analytical instrumentation.
Figure 3:
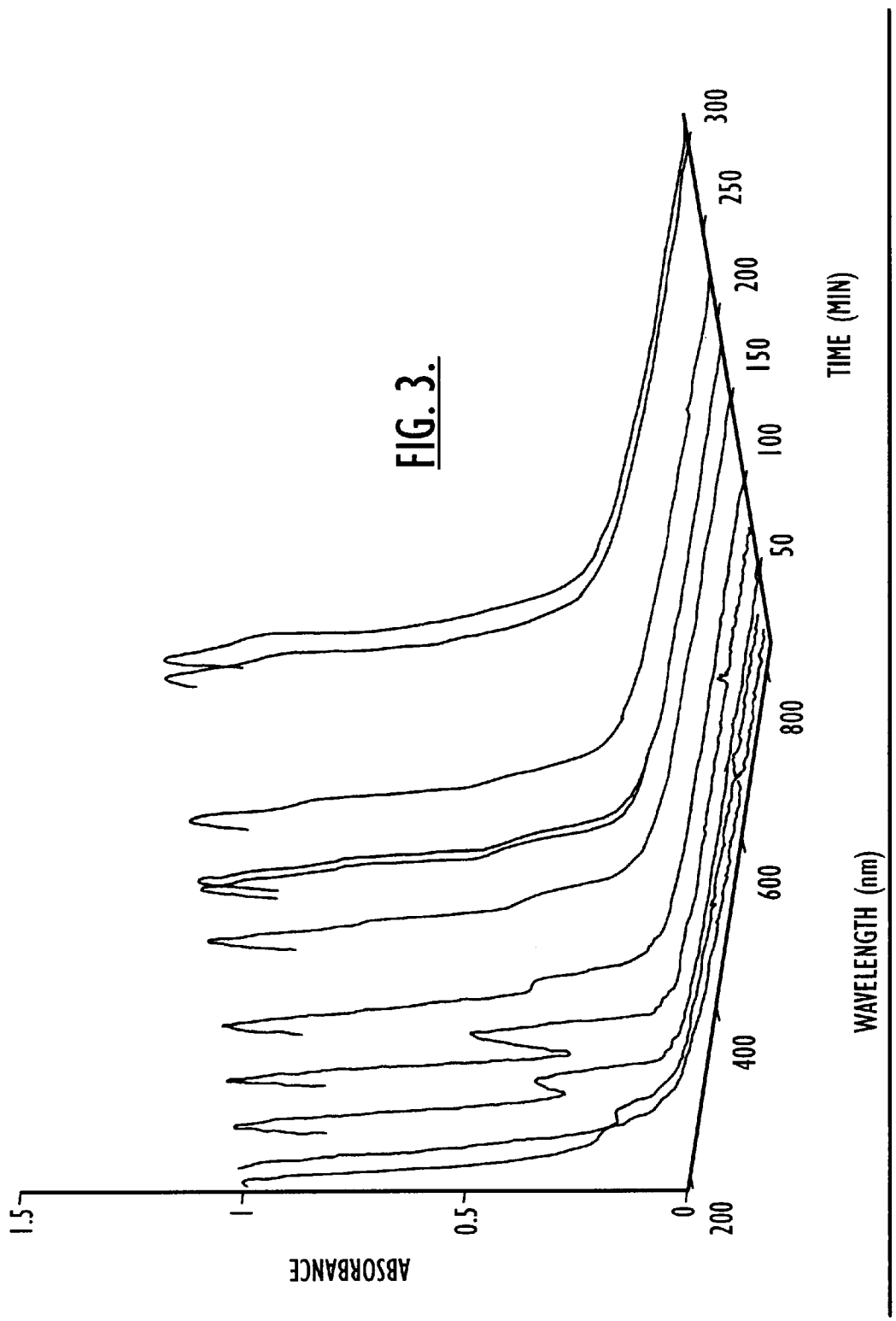
FIG. 3 is a three-dimensional plot of real-time turbimetry spectra over time for the emulsion polymerization of styrene.

A description of the preferred embodiments of the present invention will now be presented with reference to FIGS. 1–3.

The sampling and dilution system 10 (FIG. 1) comprises a network of tubing capable of carrying simultaneous dilutions in parallel fashion. The number of dilution steps is adaptable to achieve a desired dilution range.

A first dilution step comprises withdrawing from a reaction vessel 25 a sample of particle concentration $C_{s1}$ (g/ml) with a pumping unit capable of delivering $q_{s1}$ (ml/min). This flow is transported through a first tube 101 having a predetermined diameter. A second tube 102 carrying diluent $q_{d1}$ (ml/min) driven by another pumping unit 40 is then combined with the first one. The combined sample and diluent streams are allowed to mix uniformly over a third tube 103 of a predetermined diameter and length. In an alternate embodiment, an online static mixer 153 may be used to provide additional mixing.

A second dilution step comprises withdrawing fluid near the end of the mixing length of the first dilution tube 103. This third sampling channel is driven by a third pumping unit 41, withdrawing via fourth tubing 104 at $q_{s2}$ (ml/min). This stream is then combined with another diluent stream 105 at $q_{d2}$ (ml/min), and a second dilution is obtained along tubing 106. Again, a mixer 154 may be used to provide additional mixing.

This process is repeatable until a desired dilution is achieved, here shown as n.

Under ideal conditions, the following set of n equations provide an estimate for the particle concentration at each dilution step up to the nth step:

$$C_{s1}=q_{s1}/(q_{s1}+q_{d1}) \quad (1)$$

$$C_{s2}=C_{s1}q_{s2}/(q_{s2}+q_{d2}) \quad (2)$$

$$C_{sn}=C_{s(n-1)}q_{sn}/(q_{sn}+q_{dn}) \quad (n)$$

Note that as depicted the concentration at any given dilution step can be modeled as a function of the operating flow rates of both sampling and diluent streams as well as the concentration of the incoming sample. These factors can be used as optimization criteria in adapting the system to a particular reaction or composition. In addition, the sample residence time at any dilution depends primarily on the operating flow rates. Parallel dilution offers two additional advantages:

1. The combination of particle populations for continuous online measurements is minimized, a known problem in systems having mixing vessels of finite volumes. In the invention, the required mixing volume is reduced to the geometry of the tubing transporting the fluid.
2. The diluent volume required is reduced as compared with previously disclosed approaches.

In a particular embodiment shown in FIG. 2, the system 10 is integrated with a reactor setup 25 and a spectrophotometric apparatus 20, requiring a dilution in the range of 1:75,000 to 1:400,000 for latex polymerization, although this particular arrangement is not intended as a limitation, as a wide range of dilutions and analytical apparatus is anticipated for integration with the system.

Also integrated with the reactor setup 25 is a detector not requiring a diluted solution, such as a multiangle, multiwavelength detector 12 such as the type disclosed by one of us (L. H. Garcia-Rubio) previously (copending U.S. patent application Ser. No. 08/489,940, which is incorporated herein by reference).

In this embodiment, the four dilution steps are achieved with the use of a multicassette peristaltic pump 15 (Manostat) to provide the driving force for fluid flow, with a first cassette 151 and a second cassette 152 each separably controllable for fluid flow into second tube 102 and fifth tube 105, respectively (FIG. 1B). In this particular pump; up to ten pumping units (cassettes) are operated by a single shaft, and flow rates are determined by the choice of tubing diameter, shaft speed, and the choice of high- or low-flow-rate cassettes.

A first exemplary tubing arrangement is as follows:

TABLE 1

| First Exemplary Tubing Arrangement | | | |
|---|---|---|---|
| Dilution | Sampling Tube ID (in.), 1/32-in. wall | Diluent Tube ID (in.), 1/32-in. wall | Dilution Tube ID (in.), 1/16-in. wall |
| I | 1/32 | 5/32 | 1/4 |
| II | 1/32 | 5/32 | 1/4 |
| III | 1/32 | 5/32 | 1/4 |
| IV | 1/32 | 5/32 | 1/4 |

Given a shaft speed versus flow rate diagram for each diameter usable with the cassettes, the dilution of a given sample could be estimated. With flows lying in the laminar regime, they may be subject to considerable pressure drops owing to friction, which could affect mixing, an undesirable side effect. The fluid properties of the system are estimated to be similar to those of water, since waste is the continuous phase in the system and comprises more than 50% in all dilutions. The fanning factors in conjunction with the Darsy-Weisbach equation were used to calculate the pressure drops due to frictional losses. This equation, for turbulent flow, gives that for a pipe channel of length L and diameter D, transporting a fluid that has a viscosity u and density p, moving at a velocity V, the pressure drop due to frictional losses is:

$$\Delta P=2f(L/D)v^2 p$$

where $f$ is known as the fanning friction factor, which for Newtonian fluids is a function of the Reynolds number $N_{Re}$, the quotient of the surface roughness coefficient, and the pipe diameter. However, for laminar flow, the friction factor can be reduced to:

$$f=16/N_{Re}$$

For this system the Reynolds number is defined as:

$$N_{Re}=VL_c p/u$$

where $L_c$ is the characteristic length, for this case the tube diameter. With these equations we model the system 10 and assess the possibility of pressure drops causing backflow. A simulation using the tubing arrangement of Table 1 and the variables indicated in FIG. 1 provides the following:

TABLE 2

| Results of Simulation | | | | | |
|---|---|---|---|---|---|
| Stream | Tube ID (in.) | Fluid Avg. Veloc. (cm/s) | Dynamic Viscosity ($10^4$ N s/cm) | Temp. (° C.) | $\Delta$P/L ($10^2$ psia/ft) |
| qs1 | 1/32 | 9.14 | 5.43 | 50 | 7.89 |
| qd1 | 1/32 | 9.14 | 5.43 | 25 | 0.375 |
| qs2 | 1/32 | 9.14 | 9.03 | 27 | 6.55 | with pump shaft rpm=50%, total water flow rate 90 ml/min, total sample flow rate 1.28 ml/min, total water volume 7.1 gal, and total sample volume 384 ml.

An exemplary reaction of an emulsification polymerization of styrene yielded the normalized data shown in FIG. 3, illustrating the collection of real-time turbidity data over the course of the reaction. A Hewlett-Packard 8440 diode array spectrophotometer was used as the detector, which is capable of recording the complete uv-vis spectrum in less than a second. This exemplary reaction is not intended to be limiting, and it should be emphasized that the system of the present invention has utility for a wide variety of fluid entities, such as those containing particles in the micrometer to submicrometer range.

A second exemplary tubing arrangement is as follows:

TABLE 3

Second Exemplary Tubing Arrangement

| Dilution | Sampling tube ID (in.), 1/32-in. wall | Diluent tube ID (in.), 1/32-in. wall | Dilution tube ID (in.), 1.16-in. wall |
|---|---|---|---|
| I | 1/16 | 1/16 | 1/8 |
| II | 0.020 | 1/8 | 1/8 |
| III | 0.020 | 1/8 | 1/8 |
| IV | 0.020 | 1/8 | 1/8 |

This tubing arrangement was found to improve the flow and mixing performance of the system, although these parameters are not intended as limiting.

The continuous sampling and dilution system of the present invention can achieve the dilution ratios required for the use of online instrumentation such as flow-through light scattering apparatus, while remaining in the linear range of the instrument. The dilution times measured are on the order of seconds, thus suggesting that this approach is suitable for the monitoring of a large variety of processes containing particles. As discussed herein as an exemplary embodiment, the relative magnitude of the time constants for the spectrophotometer measurements and the dilution system as related to the time constants typical of emulsion polymerization processes strongly suggests that the configuration outlined herein is suitable for the monitoring and control of such systems as emulsion polymerization reactors. Other potential uses include monitoring of blood systems, and any other system containing particles in the micron to submicrometer range.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An online parallel sample dilution system comprising:
   a first dilution tube having a sample inlet, a first diluent inlet at an upstream end, a drain at a downstream end, and a first dilution outlet between the sample inlet and the drain;
   first controllable-flow-rate pumping means for introducing flowing diluent into the first dilution tube via the first diluent inlet;
   means for introducing a sample into the sample inlet, the sample and flowing diluent thereby caused to mix between the sample inlet and the first dilution outlet;
   a second dilution tube having a diluted-sample inlet in fluid communication with the first dilution outlet and a second dilution outlet downstream of the diluted-sample inlet; and
   second controllable-flow-rate pumping means for introducing flowing diluent into the second dilution tube via the diluted-sample inlet, the once-diluted sample and flowing diluent thereby caused to mix between the diluted-sample inlet and the second dilution outlet.

2. The sample dilution system recited in claim 1, wherein the first and the second pumping means comprise a unitary multicassette peristaltic pump having a first cassette and a second cassette each separably controllable for fluid flow, thereby permitting control of an extent of dilution at each respective step.

3. The sample dilution system recited in claim 1, further comprising sample pumping means for introducing the sample into the sample inlet.

4. The sample dilution system recited in claim 3, further comprising means for pumping diluted sample from the sample inlet to the first dilution outlet.

5. The sample dilution system recited in claim 1, further comprising means for sampling sample-diluent mixture within the first dilution tube between the sample inlet and the first dilution outlet.

6. The sample dilution system recited in claim 1, further comprising means for sampling diluted sample-diluent mixture within the second dilution tube between the diluted sample inlet and the second dilution outlet.

7. The sample dilution system recited in claim 1, further comprising means for transporting twice-diluted sample from the outlet in the second dilution tube to an analytical apparatus.

8. The sample dilution system recited in claim 1, wherein the first and the second dilution tubes comprise a first and a second variable-diameter tube, thereby permitting control over dilution achievable therein.

9. The sample dilution system recited in claim 1, further comprising:
   a plurality of additional dilution tubes, each in fluid communication with a preceding a following dilution tube, for providing additional dilution to the sample; and
   a plurality of diluent introducing means, one each for flowing diluent into each additional dilution tube via a diluent inlet;
   a final dilution tube, in fluid communication with the last of the additional dilution tubes, having a diluted sample outlet and a diluent inlet; and
   a final diluent introducing means for flowing diluent into the final dilution tube diluent inlet, wherein a final concentration of the sample emerging from the diluted sample outlet is approximately:

$$C_{sn}=C_{s(n-1)}q_{sn}/(q_{sn}+q_{dn}),$$

where $C_{sn}$ represents a sample concentration at an nth dilution step, $q_{sn}$ represents a sample flow rate at the nth step, and $q_{dn}$ represents a diluent flow rate at the nth step.

10. An online parallel sample dilution system comprising:
   a first dilution tube having a sample inlet, a first diluent inlet at an upstream end, a drain at a downstream end, and a first dilution outlet between the sample inlet and the drain;
   fluid mixing means positioned and adapted to provide additional mixing of the sample-diluent mixture within the first dilution tube between the sample inlet and the first dilution outlet;

first means for introducing flowing diluent into the first dilution tube via the first diluent inlet;

means for introducing a sample into the sample inlet, the sample and flowing diluent thereby caused to mix between the sample inlet and the first dilution outlet;

a second dilution tube having a diluted-sample inlet in fluid communication with the first dilution outlet and a second dilution outlet downstream of the diluted-sample inlet; and second means for introducing flowing diluent into the second dilution tube via the diluted-sample inlet, the once-diluted sample and flowing diluent thereby caused to mix between the diluted-sample inlet and the second dilution outlet.

11. The sample dilution system recited in claim 10, further comprising fluid mixing means positioned and adapted to provide additional mixing of the diluted sample-diluent mixture within the second dilution tube between the diluted sample inlet and the outlet.

12. A method for diluting a concentrated sample comprising the steps of:

introducing diluent into a first diluent tube and a second diluent tube with a controllable-flow-rate pump;

introducing the sample into the first diluent tube;

permitting the sample and diluent to mix along a length of the first diluent tube;

introducing a portion of the sample-diluent mixture into the second diluent tube;

permitting the sample-diluent mixture portion and the diluent to mix along a length of the second diluent tube to produce a twice-diluted sample; and extracting a portion of the twice-diluted sample from the second diluent tube.

13. A method of achieving a desired dilution level of a concentrated sample comprising the steps of:

providing a first diluent tube and a second diluent tube, each having a variable diameter, for flowing diluent therethrough at correspondingly variable flow rates;

introducing the sample into the first diluent tube;

pumping diluent through the first and the second diluent tube with the use of a first and a second variable-speed pumping means, respectively;

permitting the sample and diluent to mix along a length of the first diluent tube;

introducing a portion of the sample-diluent mixture into the second diluent tube;

permitting the sample-diluent mixture portion and the diluent to mix along a length of the second diluent tube to produce a twice-diluted sample;

extracting a portion of the twice-diluted sample from the second diluent tube;

measuring a concentration of the twice-diluted sample; and adjusting at least one of the variable-speed pumping means and the diameters of the first and the second dilution tubes to achieve the desired concentration of the twice-diluted sample.

14. A system for monitoring a chemical reaction in real time, the system comprising:

a vessel for containing reactants undergoing the chemical reaction to form a reaction mixture;

a device for diluting a sample of the reaction mixture comprising:

a first dilution tube having a sample inlet in fluid communication with the reaction vessel, a first diluent inlet at an upstream end, a drain at a downstream end, and a first dilution outlet between the sample inlet and the drain;

first controllable-flow-rate pumping means for introducing flowing diluent into the first dilution tube via the first diluent inlet;

means for introducing the sample into the sample inlet, the sample and flowing diluent thereby caused to mix between the sample inlet and the first dilution outlet;

a second dilution tube having a diluted-sample inlet in fluid communication with the first dilution outlet and a second dilution outlet downstream of the diluted-sample inlet; and second controllable-flow-rate pumping means for introducing flowing diluent into the second dilution tube via the second diluent inlet, the once-diluted sample and flowing diluent thereby caused to mix between the diluted-sample inlet and the outlet to form a twice-diluted sample; and an analytical device for measuring a characteristic parameter of the sample having means for receiving a portion of the twice-diluted sample, the analytical device for monitoring the chemical reaction.

15. A method for diluting a concentrated sample for analysis, the method comprising the steps of:

withdrawing from a reaction vessel a sample having a concentration represented by $C_{s0}$ at a flow rate of $q_{s1}$;

combining the withdrawn sample with a first stream of diluent flowing at a flow rate of $q_{d1}$ introduced by a controllable-flow-rate pump;

permitting the sample and diluent to mix to provide a concentration of $C_{s1}$;

withdrawing a portion of the flowing sample-diluent mixture at a flow rate of $q_{s2}$;

combining the withdrawn sample-diluent mixture with a second stream of diluent flowing at a flow rate of $q_{d2}$ introduced by a controllable-flow-rate pump;

permitting the sample-diluent mixture and diluent to mix to provide a concentration of $C_{s2}$; and withdrawing a portion of the flowing twice-diluted sample for analysis.

16. The method recited in claim 15, further comprising the step of adjusting at least one of the $q_{s1}$, $q_{s2}$, $q_{d1}$, and $q_{d2}$ in order to achieve a desired final concentration, the final concentration approximated by:

$$C_{s2}=C_{s0}q_{s1}q_{s2}/(q_{s1}+q_{d1})(q_{s2}+q_{d2}).$$

* * * * *